(12) United States Patent
Larsen et al.

(10) Patent No.: US 8,877,717 B2
(45) Date of Patent: Nov. 4, 2014

(54) ANTI-DIABETIC EXTRACT OF ROOIBOS

(75) Inventors: Peter Mose Larsen, Odense S (DK);
Stephen John Fey, Blommenslyst (DK);
Johan Louw, Tygerberg (ZA); Lizette Joubert, Pretoria (ZA)

(73) Assignee: Zadec ApS, Hellerup (DK)

( * ) Notice: Subject to any disclaimer, the term of this patent is extended or adjusted under 35 U.S.C. 154(b) by 709 days.

(21) Appl. No.: 12/531,035

(22) PCT Filed: Mar. 11, 2008
(Under 37 CFR 1.47)

(86) PCT No.: PCT/EP2008/052861
§ 371 (c)(1),
(2), (4) Date: Jan. 15, 2010

(87) PCT Pub. No.: WO2008/110551
PCT Pub. Date: Sep. 18, 2008

(65) Prior Publication Data
US 2011/0275579 A1   Nov. 10, 2011

Related U.S. Application Data

(60) Provisional application No. 60/894,258, filed on Mar. 12, 2007.

(51) Int. Cl.
*A61K 31/70* (2006.01)
*A61K 31/7004* (2006.01)
*A61K 36/48* (2006.01)

(52) U.S. Cl.
CPC ............. *A61K 36/48* (2013.01); *A61K 31/7004* (2013.01)
USPC ........................................................ 514/23

(58) Field of Classification Search
None
See application file for complete search history.

(56) References Cited

U.S. PATENT DOCUMENTS

| 6,572,897 | B1 | 6/2003 | Gorsek |
| 2010/0222423 | A1 | 9/2010 | Frank et al. |

FOREIGN PATENT DOCUMENTS

| DE | 101 18 695 A1 | 10/2002 |
| JP | 5-246875 | 9/1993 |
| JP | 5-271059 | 10/1993 |
| JP | 2003-171305 | 6/2003 |
| JP | 2003-171305 A * | 6/2003 |
| JP | 2003171305 * | 6/2003 |
| JP | 2007-0070263 | 10/2008 |
| WO | WO 00/15174 | 3/2000 |

OTHER PUBLICATIONS

Joubert et al, "Superoxide anion and α, α-diphenyl-β-picrylhydrazyl radical scavenging capactiy of rooibos (Aspalathus linearis) aqueous extracts, crude phenolic fractions, tannin and flavonoids,", *Food Research International* (2004) 37:133-138. XP002375310.
Jaganyi et al., "Rooibos tea: equilibrium and extraction kinetics of aspalathin," *Food Chemistry* (2003) 83: 121-126. XP002484684.
Joubert, L., "Instant Rooibos Tea," *Food Review* (1991) 18 (5):24-27. XP009072758.
Form PCT/ISA/206 for International Application PCT/EP2008/052861.

* cited by examiner

*Primary Examiner* — Traviss C McIntosh, III
(74) *Attorney, Agent, or Firm* — Merchant & Gould P.C.

(57) ABSTRACT

Novel and useful compositions derived from rooibos for treating diabetes are provided. The present invention is particularly concerned with the treatment of Type 2 diabetes. The invention provides a new use for aspalathin and rutin and compositions containing them for use in the prevention and treatment of diabetes. The invention provides an anti-diabetic agent, an anti-diabetic composition containing the anti-diabetic agent, a foodstuff or beverage containing the anti-diabetic agent, a method for preventing or treating diabetes or impaired glucose tolerance, and a method of decreasing blood glucose level. The anti-diabetic agent may be an extract from rooibos (*Aspalathus* spp.), aspalathin as such or in combination with rutin.

14 Claims, 15 Drawing Sheets

ANTI-DIABETIC EXTRACT OF ROOIBOS

This application is a National Stage Application of PCT/EP2008/052861, filed Mar. 11, 2008, which claims benefit of Ser. No. 60/894,258, filed Mar. 12, 2007 in the United States and which application(s) are incorporated herein by reference. To the extent appropriate, a claim of priority is made to each of the above disclosed applications.

FIELD OF THE INVENTION

The present invention relates to a plant extract for use as a hypoglycemic agent, i.e. for lowering blood glucose levels in mammals that are pre-diabetic or have type 2 diabetes (T2D) or type 1 diabetes (T1D).

BACKGROUND OF THE INVENTION

The non-communicable disease, diabetes mellitus, can be divided into two major types, viz. type 1 diabetes (T1 D) and type 2 diabetes (T2D). T1 D is characterized by β-cell autoimmunity. In T2D, the pancreatic β-cells produce insufficient insulin, and the peripheral tissues (liver, muscle and adipose tissue) are "resistant" to actions of insulin, i.e. glucose uptake is inefficient in these target tissues. The β-cells are also often destroyed in late stages of T2D making the patient dependant on insulin treatment. In diabetes patients, approximately 5-10% are type 1 and 90-95% are type 2 diabetic. Major diabetic complications include retinopathy, cerebrovascular disease, coronary heart disease, neuropathy, peripheral vascular disease, ulceration and amputation. Thus diabetes affects several organs and tissues throughout the body. Factors that contribute to the development of diabetes include ethnicity (where certain population groups have an increased incidence of T2D, particularly if they have migrated), obesity, a high fat diet, the intrauterine environment, insulin resistance and specific candidate genes.

The incidence of type 2 diabetes is increasing worldwide. Although genetic factors may play a role, life-style changes such as the adoption of a Western diet, high in fat, leads to obesity which can be a factor also contributing to the increase of this disease. Life-style factors, such as increased fat intake and reduced exercise, have been shown to be associated with obesity and insulin resistance (Lipman et al., 1972; Lovejoy and DiGirolamo, 1992). In rats, high fat feeding induces a state of insulin resistance associated with diminished insulin-stimulated glycolysis and glycogen synthesis (Kim et al., 2000). This disease is a result of the peripheral insulin-responsive tissues, such as muscle and adipose tissue, displaying a significant decrease in response to insulin resulting in an increase in circulating glucose and fatty acids in the blood. The low response to insulin results in a decrease in glycolysis which in turn initiates gluconeogenesis and glycogenolysis in the liver, both of which are "switched off" by insulin under normal conditions. Pancreatic β-cells are able to cope with the initial insulin resistant phase by producing an excess of insulin and increasing the amount of insulin secreted (Pirol et al., 2004). The resulting hyperinsulinaemia to maintain normoglycaemia eventually brings about cell dysfunction (Khan, 2003) leading to overt diabetes. It is evident that type 2 diabetes is dependent on insults occurring both at peripheral as well as the cellular level (Khan et al., 2000).

It is well established that insulin resistance and subsequent β-cell failure are major factors influencing the progression from normal glucose tolerance, through impaired glucose tolerance, to T2D. Lifestyle changes associated with the move from a rural to an urban area lead to an increase in obesity in urban black South Africans and this is associated with insulin resistance, which is another feature of T2D. To compensate for the insulin resistant state, β-cells produce more insulin and this leads to a higher demand on the already overworked β-cells which will result in β-cell exhaustion and ultimately β-cell failure.

There were an estimated 30M people with diabetes in the world in 1985. By 1995 the number had increased to 135M. The latest World Health Organization (WHO) estimate is that 300M people will have diabetes in 2025, an increase of 122%. This is in agreement with the International Diabetes Federation (IDF) estimation, in 2025, of 333M people with diabetes (6.3% prevalence), while 472M will be diagnosed with impaired glucose tolerance (IGT; 9% prevalence). There will be an estimated increase of 42% from 51M to 72M, for the developed world (where there is an increase in the incidence of overweight and obese individuals, increasing their risk for becoming diabetic) and an increase of 170% from 84M to 228M for developing countries (due to a myriad of factors including dietary changes, increased physical activity and rapid urbanization). Thus while diabetes was previously considered a western life style disease affecting people in the developed countries, current trends suggest that by 2025 over 75% of all people with diabetes will be in the developing world. Another contributing factor to the increased incidence of diabetes in the developing world is developmental programming. In many parts of the developing world, people are often exposed to a poor diet (undernutrition) in utero followed by overnutrition postnatally which has been shown to predispose individuals to developing T2D. Furthermore, a total of 1.1 billion people are currently overweight, and 320M people are obese (IDF). This emphasizes the huge global economic burden of obesity, and as obesity is a major risk factor for developing diabetes, this may potentially further exacerbate the already huge economic burden associated with diabetes.

Conservative estimates for South Africa, based on minimal data, predict an increase from 5.6M in 2000 to over 8M in 2010. The largest increase is most likely to be in the black populations due to urbanisation, since this is accompanied by lifestyle and dietary changes from a low fat to a high fat diet. Figures in 1998 showed urban black South Africans to have an escalating incidence of T2D with the age-adjusted prevalence approaching 8% (Levitt, 1993), almost double the figure of 4.2% published in 1974 (Joffe & Seftel). In 1996 data for the top twenty causes of deaths in South Africa (Bradshaw et al, 1996) revealed diabetes to be the $10^{th}$ in males and $7^{th}$ in females. However, complications of diabetes, such as ischaemic heart disease and other cardiovascular and kidney complications contribute significantly to the number of deaths and adjusted figures could place diabetes in the top three or four causes of death in South Africa. The incidence of T2D is greater than HIV in SA, thus T2D warrants national attention.

Diabetes is an expensive disease and, although information on the cost of treating diabetics in South Africa is not available, there are many indirect costs. These include a reduction in the quality of life, the ability to contribute to the community and the workforce and its effect on the economy. This is exacerbated by an increased cost to Medical Aid Schemes resulting in increased Medical Aid premiums. Diabetes also affects the economy directly. In the absence of diabetes related financial data in South Africa, published data from the UK show that with more than 1.5M adults in the UK currently diagnosed with diabetes and its complications, the total National Health Service (NHS) cost is £5.2 billion each year, which is 9% of the total NHS budget. In the USA, the estimated direct costs are US$ 44 billion and, with loss of productivity, this figure increased to US$ 98 billion. Similar figures are available for many other countries.

T2D is diagnosed by raised levels of plasma glucose. However, our previous research has shown that by the time blood glucose levels increase, serious damage has already occurred in the cardiovascular system and the pancreas. Following diagnosis of diabetes by raised blood glucose levels, therapies such as diet and exercise and/or available medication can result in a temporary improvement in plasma glucose levels but cannot halt the progression of the disease. The rate of failure of these therapies is associated with the rate of continuing β-cell decline. Current treatment involves insulin injection or stimulating insulin release and/or action by medication.

There are many theories for explaining the impairment of insulin production by the pancreas that leads to the diabetic condition. Reference is made to two papers: "Mechanisms of pancreatic beta-cell destruction in type I diabetes" by Nerup J, Mandrup-Poulsen T, Molvig J, Helqvist S, Wogensen L, Egeberg J. published in Diabetes Care. 1988; 11 Suppl 1:16-23; and the second entitled "Autoimmune Imbalance and Double Negative T Cells Associated with Resistant, Prone and Diabetic Animals", Hosszufalusi, N., Chan, E., Granger, G., and Charles, M.; J Autoimmun, 5: 305-18 (1992). These papers show that inflammation of the pancreatic islets interrupts insulin production. Specifically, the insulin producing β-cells in the pancreatic islets are destroyed by immune attack. Such β-cell destruction is recognized as being due to attack by several types of immune cells including NK (natural killer) cells and double negative T-Lymphocytes.

Diabetes is considered to be insidious, since there is no known cure. Various treatments, however, have been used to ameliorate diabetes. For example, dietetic measures have been employed to balance the relative amounts of proteins, fats, and carbohydrates in a patient. Diabetes education and awareness programmes have also been implemented in several countries. In addition, diabetic conditions of moderate or severe intensity are treated by the administration of insulin. Also, prescription drugs such as "Glucoside" have been employed to rejuvenate impaired insulin production in adult onset diabetics. Other drugs are used to modulate the effectiveness of insulin. In any case, treatment of either juvenile or adult onset diabetes, has achieved only partial success. This is due to most agents targeting either improved beta-cell function or reducing insulin resistance, with the effect attenuating as the disease progressively worsens. Thus patients require the use (often daily) of a combination of agents to control the disease.

Biguanides, such as metformin, became available for treatment of type 2 diabetes in the late 1950s, and have been effective hypoglycaemic agents ever since (Vigneri and Goldfine, 1987). Little is known about the exact molecular mechanism of these agents. As an insulin sensitizer, metformin acts predominantly on the liver, where it suppresses glucose release (Goldfine, 2001). Metformin has also been shown to inhibit the enzymatic activity of complex I of the respiratory chain and thereby impairs both mitochondrial function and cell respiration, and in so doing decreasing the ATP/ADP ratio which activates AMP activated protein kinases causing catabolic responses on the short term and insulin sensitization on the long term (Brunmair et al., 2004; Tiikkainen et al., 2004). This drug has been proven effective in both monotherapy and in combination with sulfonylureas or insulin (Davidson and Peters, 1997). Diabetes in the young is a global phenomenon that is increasing in incidence. Some key transcription factors, important for beta-cell development, differentiation and function, are implicated in diabetes in the young. Some of these are direct targets of current therapeutic agents. The cost of current diabetic drugs is very high and the development of more affordable alternative therapies would be an advantage. The global burden of T2D is huge. Strategic action is required to endure affordable diabetes treatment to improve the quality of life of those individuals affected. This is particularly true for the developing world. It is for this reason that scientists are investigating the efficacy of indigenous plant extracts in their own country.

Rooibos, (scientific name *Aspalathus linearis*) is a member of the legume family of plants and is used to make a tisane (herbal tea). *Aspalathus linearis* is a unique South-African fynbos plant cultivated for the production of Rooibos tea. Rooibos tea is made from the stalks and leaves of the plant, which are shredded, bruised and moistened, followed by a long period of open air oxidation ("fermentation") and sun-drying to allow for development of the characteristic Rooibos colour and flavour. Processed plant material is then sieved and packaged as loose leaves or in tea bags. This processed material is referred to as "fermented Rooibos tea". "Green" Rooibos tea refers to the unoxidised ("unfermented") Rooibos plant material that is processed in such a manner as to prevent or limit oxidative changes Health-promoting properties associated with Rooibos tea include relief of insomnia, nervous tension, stomach cramps and allergic symptoms. Flavonoids in Rooibos tea have strong antioxidant and free radical scavenging activities and have the potential to act as anti-carcinogenic and anti-arteriosclerotic agents. Rooibos tea and products derived therefrom are valuable for use in food/nutraceutical, pharmaceutical and/or cosmetic industry.

At present, Type 1 diabetic patients are treated with insulin, while the majority of Type 2 diabetic patients are treated with hypoglycemic agents, such as sulfonylureas that stimulate β-cell function, with other agents that enhance the tissue selectivity of the patients towards insulin, or with insulin itself. Unfortunately, the use of insulin currently requires multiple daily doses, normally administered by self-injection, with determination of the proper dosage of insulin requiring frequent estimations of the sugar in urine or blood, performed either by the patient or the administering physician. The unintended administration of an excess dose of insulin can result in hypoglycemia, with adverse effects ranging from mild abnormalities in blood glucose to coma, or even death. Although hypoglycemic agents such as sulfonylureas have been employed widely in the treatment of NIDDM, this treatment is, in many instances, not completely satisfactory. Where existing treatments prove ineffective in normalizing blood sugar levels of patients, there is an increased risk of acquiring diabetic complications. Also, many patients gradually lose the ability to respond to treatment with sulfonylureas and are thus gradually forced into insulin treatment. Since many extant forms of diabetic therapy have proven ineffective achieving satisfactory glycemic control, there continues to be a great demand for novel therapeutic approaches.

As a result of its adipogenic effect, insulin has the undesirable effect of promoting obesity in patients with type 2 diabetes. (See, Moller, D. E. (2001) *Nature* 414:821-827). Unfortunately, other anti-diabetic drugs, including metformin, which are currently being used to stimulate glucose transport in patients with type 2 diabetes also possess adipogenic activity. Thus while current drug therapy may provide reduction in blood sugar, it often promotes obesity. Accordingly, new compositions and methods for treating hyperglycemia are desirable. Compositions that stimulate glucose uptake without generating concomitant adipogenic side effects are especially desirable.

SUMMARY OF THE INVENTION

In accordance with the present invention novel and useful compositions derived from rooibos for treating diabetes are provided. The present invention is particularly concerned with the treatment of Type 2 diabetes and the corresponding anti-diabetic agents. The invention provides a new use for aspalathin and rutin and compositions containing them for use in the prevention and treatment of diabetes. The invention provides an anti-diabetic agent, an anti-diabetic composition containing the anti-diabetic agent, a foodstuff or beverage containing the anti-diabetic agent, kits based on the anti-diabetic agent, a method for preventing or treating diabetes or impaired glucose tolerance, and a method of decreasing blood glucose level. The anti-diabetic agent may be an extract from rooibos (*Aspalathus* spp.), aspalathin as such or in combination with rutin.

The treatment of the present invention was discovered because the inventors found that a steam or aqueous extract of rooibos (*Aspalathus* ssp) was effective in controlling blood sugar. For the medical use in accordance with the present invention the plant is gathered, dried, and combined with a solvent such as water and/or an alcohol, preferably ethanol.

It has surprisingly been found that the plant extract of the present invention exhibit a superior antidiabetic effect when administered in an amount from about 1 milligram to about 5 milligrams, preferably to about 2.5 milligrams, per kilogram body weight.

Accordingly, in a first aspect the present invention relates to an anti-diabetic composition comprising an aqueous extract of plants of the genus *Aspalathus*, preferably *Aspalathus linearis*, said composition administered in a dose range of 1-5 mg/kg, preferably to about 2.5 mg/kg, body weight.

In another aspect of the invention there is provided a method for isolating a therapeutic extract of the plant *Aspalathus* with anti-diabetic effects, said method comprising the steps of:
(a) providing *Aspalathus* plants or portions thereof,
(b) combining said plants or portions thereof with a nontoxic solvent, such as water and/or an alcohol, preferably ethanol, appropriate for solubilizing said plant extract,
(c) recovering said plant extract, and
(d) optionally drying.

The present inventors have found that administering an extract of the plant genus *Aspalathus* allows for treatment of diabetes, and in particular of early stages of diabetes, also referred to as pre-diabetic states.

Thus, the present invention relates to compositions derived from the plant genus *Aspalathus* and methods for treating subjects who are hyperglycemic, particularly subjects with Type 2 diabetes as well as diabetic subjects who are overweight. In a preferred embodiment the present invention provides a *Aspalathus* plant extract for treating subjects who are hyperglycemic.

The present invention also provides a method for reducing blood glucose levels in subjects who are hyperglycemic. The method comprises administering the *Aspalathus* plant extract to the hyperglycemic subject. Although it is possible to administer the extract to the subject by injection, the preferred method of administration involves oral administration. The method is useful for treating subjects who are hyperglycemic, as well as subjects with diabetes mellitus. The method is especially useful for treating overweight subjects with Type 2 diabetes, and in particular early stages thereof.

The present inventors have also found that the extracts of the invention increase the activity of Glut4 and Glu2 in an independent manner so that in some instances both of these glucose transporters are more active whereas in other instances only one of them are active. Accordingly, the present invention also provides a method of controlling diabetes mellitus in a mammal comprising the step of administering to the mammal an extract of *Aspalathus* in an amount that increases the activity of Glut4 and/or Glut2.

As a consequence thereof the present invention is also useful for screening active ingredients of the extracts. Thus, the present invention furthermore provides a method of screening specific compounds of the extract for anti-diabetic activity in a mammal comprising the step of determining which compounds that increase the activity of Glut4 and/or Glut2.

The treatment of the present invention was discovered because the inventors found that a steam or aqueous extract of *Aspalathus* was effective in controlling blood sugar. For use the plant is gathered, dried, and combined with boiling water. The extract is then taken orally by a patient on a periodic basis. *Aspalathus* is known to be rich in flavonoids and other secondary plant products. The extracts as well as the pure active components herein described have been administered to both diabetic rats and monkeys; the results clearly and unambiguously show that such extracts will have a significant impact on the future treatment of diabetes in humans.

Specific flavonoids have been extracted and fractionated from *Aspalathus* and administered to diabetic rats with results similar to those produced by the extract. The flavonoids specifically used were aspalathin and rutin. It was then discovered that these flavonoids are most effective in combination. What was truly surprising was the discovery that aspalathin alone or in combination with rutin, in particular, is effective in lowering the blood sugar and generally alleviating diabetic symptoms in both T1 D and T2D rats. This result was unexpected because conventional wisdom teaches that these two forms of diabetes have basically different causes (β-cell destruction and insulin resistance in muscles respectively).

DETAILED DESCRIPTION OF THE INVENTION

Figure 1:
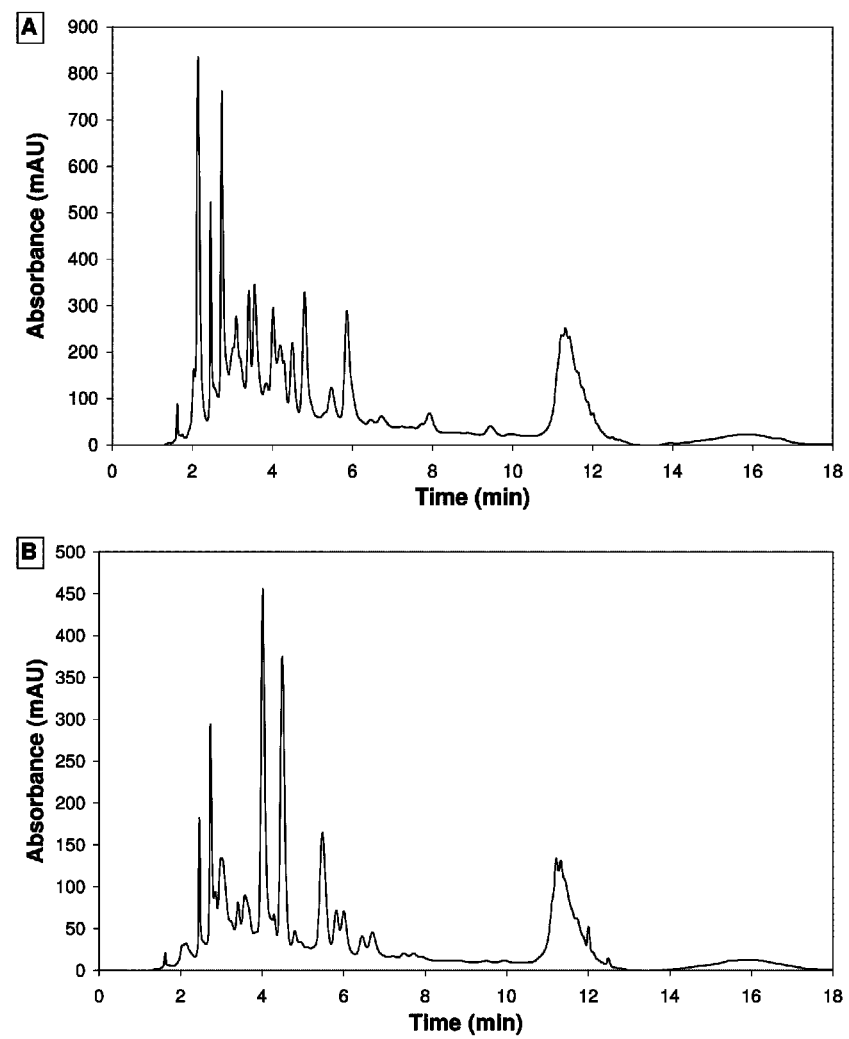
FIG. 1. Shows an HPLC fingerprint of aqueous extracts of rooibos plant material used for preparation of GMP ARC 61 (A=chromatogram at 288 nm; B=chromatogram at 320 nm).
Figure 2:
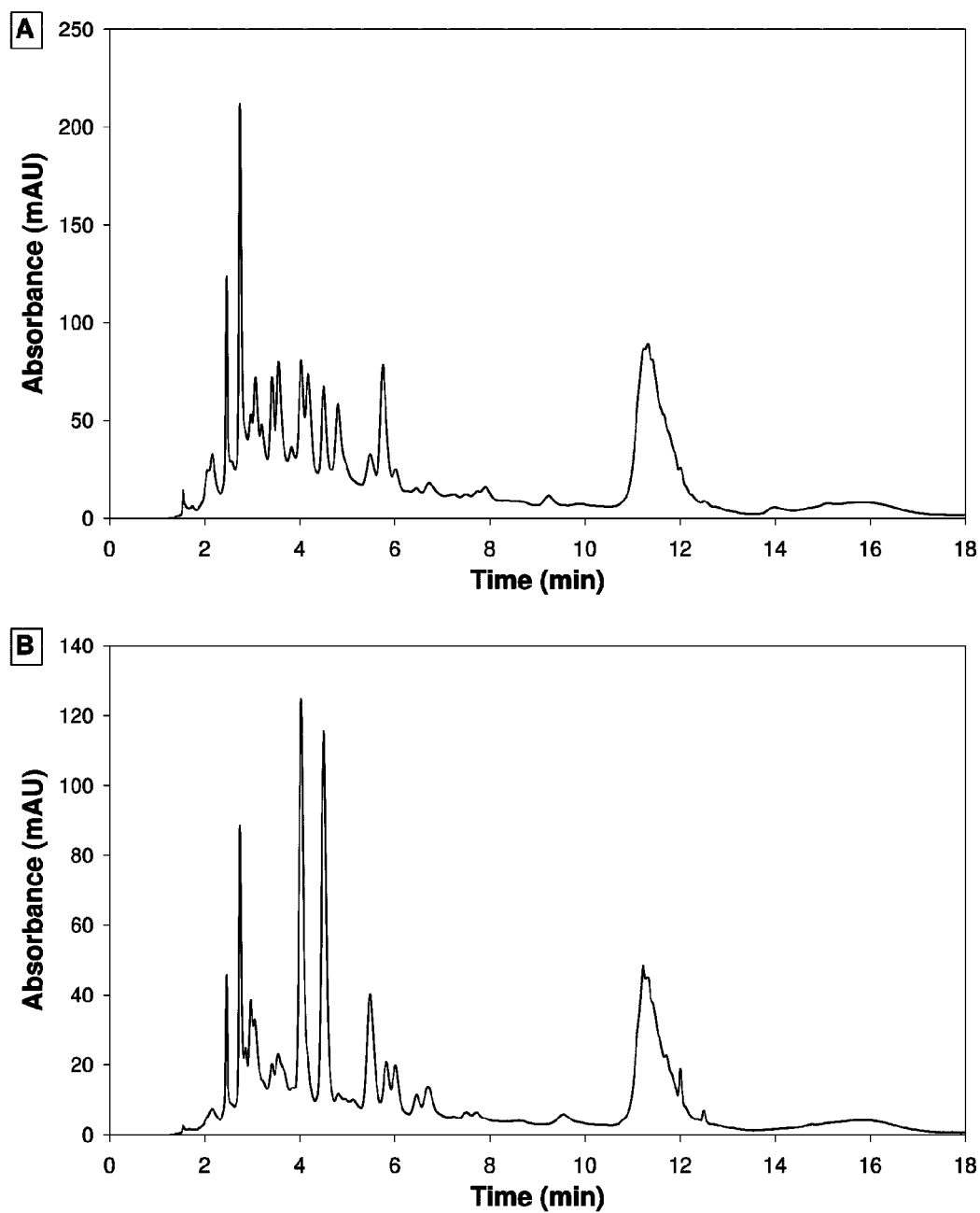
FIG. 2. Shows an HPLC fingerprint of GMP ARC61 (A=chromatogram at 288 nm; B=chromatogram at 320 nm).

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide treatment of both insulin-dependent and non-insulin dependent diabetes through the administration of flavonoids particularly through the administration of a plant extract in accordance with the present invention.

DEFINITIONS

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include impaired glucose tolerance, which is a metabolic stage intermediate between normal glucose homeostasis and diabetes. The guidelines for diagnosis for Type 2 diabetes and impaired glucose tolerance have been outlined by the American Diabetes Association (see, e.g., The Expert Committee on the Diagnosis and Classification of Diabetes Mellitus, Diabetes Care, (1999) Vol 2 (Suppl 1): S5-19).

The term "symptom" of diabetes, includes, but is not limited to, polyuria, polydipsia, and polyphagia, hyperinsulinemia, and hyperglycemia as used herein, incorporating their common usage. For example, "polyuria" means the passage of a large volume of urine during a given period; "polydipsia" means chronic, excessive thirst; "polyphagia" means excessive eating, and hyperinsulinemia means elevated blood levels of insulin. Other symptoms of diabetes include, for example, increased susceptibility to certain infections (especially fungal and staphylococcal infections), nausea, and ketoacidosis (enhanced production of ketone bodies in the blood).

Dosage

The rooibos (*Aspalathus* ssp.) plant extract is administered to the subject in a therapeutically effective amount. As used herein, the term "therapeutically effective amount" means the total amount that is sufficient to show a meaningful benefit, i.e., a reduction in the subject's blood glucose levels. The dosages of the plant extract needed to obtain a meaningful result, can be determined in view of this disclosure by one of ordinary skill in the art by running routine trials with appropriate controls. Comparison of the appropriate treatment groups to the controls will indicate whether a particular dosage is effective at reducing the subject's blood glucose levels. When orally administered the extract should be in doses of at least 0.1 mg/kg body weight, preferably at least 1 mg/kg, more preferably at least 2.5 mg/kg, even more preferably at least 5 mg/kg, most preferably at least 25 mg/kg, such as at least 50 mg/kg, at least 75 mg/kg, at least 100 mg/kg, at least 250 mg/kg, and at least 500 mg/kg.

The amount of the plant extract required will depend upon the nature and severity of the condition being treated, and on the nature of prior treatments which the subject has undergone. Ultimately, the dosage will be determined using clinical trials. Initially, the clinician will administer doses that have been derived from animal studies. An effective amount can be achieved by one administration of the composition. Alternatively, an effective amount is achieved by multiple administration of the composition to the subject. In vitro, the biologically effective amount, i.e., the amount sufficient to induce glucose uptake, is administered in two-fold increments, to determine the full range of activity. The efficacy of oral, subcutaneous and intravenous administration is determined in clinical studies. Although a single administration of the extract may be beneficial, it is expected that multiple doses will be preferred.

Delivery

Administration of the rooibos plant extract preferably is by oral administration. Although less preferred, the extract may also be administered by injection. Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like. The extract may be administered in the form of pills (powder or concentrated liquid in capsules), or powder form (e.g. dried powder but pressed into grains) that can be consumed after putting into water (similar to drinking tea or coffee).

Formulations suitable for parenteral administration conveniently comprise a sterile preparation of the active compound in, for example, water for injection, saline, a polyethylene glycol solution and the like, which is preferably isotonic with the blood of the recipient. Useful formulations also comprise concentrated solutions or solids containing the rooibos plant extract which upon dilution with an appropriate solvent give a solution suitable for parenteral administration.

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of the rooibos plant extract required to be effective for any indicated condition will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular extract to be administered. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

The composition comprises a biologically effective amount of the rooibos plant extract, and, optionally, a relatively inert carrier. Many such carriers are routinely used and can be identified by reference to pharmaceutical texts. The acceptable carrier is a physiologically acceptable diluent or adjuvant. The term physiologically acceptable means a non-toxic material that does not interfere with the effectiveness of the analog. The characteristics of the carrier will depend on the route of administration and particular compound or combination of compounds in the composition. Preparation of such formulations is within the level of skill in the art. The composition may further contain other agents that either enhance the activity of the analog or complement its activity. The composition may further comprise fillers, salts, buffers, stabilizers, solubilizers, and other materials well known in the art.

Concerning the flavonoids in accordance with the present invention the following should be mentioned.

Aspalathin is a natural molecule found in rooibos. The molecule is classified as a flavonoid, one of at least four thousand known flavonoids. Aspalathin is the principal monomeric polyphenol occurring in the leaves of *Aspalathus linearis*. The chemical name of Aspalathin is 3'-C-fl-D-glucopyranosyl-2',3,4,4',6'-pentahydroxydihydrochalcone (I) and has the structure:

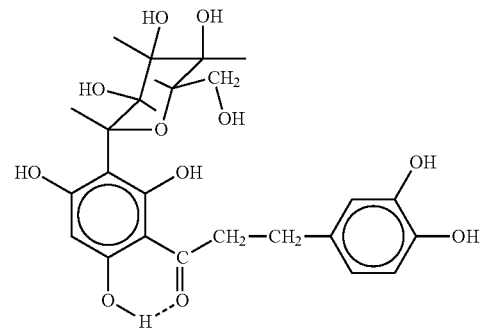

Rutin is also a natural molecule found in rooibos.

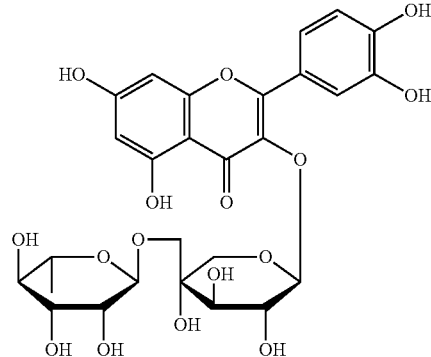

Other related compounds with a backbone of 2-phenyl-chromen-4-one (2-phenyl-1-benzopyran-4-one), so called flavones:

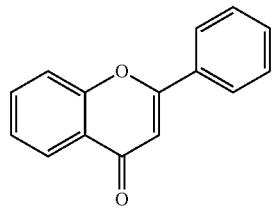 [SMILES: O=c1cc(-c2ccccc2)oc2ccccc12]

are present in rooibos and all of them exert some kind of antidiabetic activity (verified in vitro).

Different species of rooibos contain these, or similar flavonoids, albeit in different proportions. Experiments with diabetic test animals (rats) were carried out. The rooibos extract of the present invention was effective in controlling blood glucose in these model systems. Further, the administration of synthetic versions of the flavonoids were also effective at lowering glucose levels. However, it was found by the present inventors that a combination of Aspalathin with the other flavonoids, especially rutin, results in an enhanced (synergistic) effect in that blood glucose can be maximally lowered with a lower overall flavonoid dose. The effect is most pronounced when the molar concentration of aspalathin is at least twice that of rutin. In addition thereto it was found that the antidiabetic effect of these flavonoids is greater when present in the plant extract of the present invention than in their pure form.

According to the present invention, and as hereinbefore and hereafter mentioned: "diabetes" preferably refers to non-insulin dependent diabetes (type 2); "anti-diabetic" means the activity useful for the "treatment" of "diabetes", which includes the prevention of the development of diabetes, and/or the treatment of established diabetes; it also includes the prevention of the causes of diabetes, and/or the decrease or disappearance of its symptoms and/or consequences.

In particular, it has been found that compounds of the invention have at least the following double therapeutic effect:

i) the prevention of diabetes, since the compounds of the invention can treat impaired glucose tolerance; and ii) the actual treatment of established diabetes since the compounds of the invention can decrease the blood glucose level.

Preferably, the extract of the present invention comprises as an active ingredient a compound having the essential features of aspalathin and/or a pharmaceutically acceptable salt or prodrug thereof. More preferably the extract also comprises as an active ingredient a compound having the essential features of rutin. Most preferably the molar concentration of aspalathin is at least twice that of rutin.

According to a further aspect, the invention also concerns the said extract for use as a medicament having anti-diabetic activity.

The invention also extends to a pharmaceutical composition having anti-diabetic activity comprising an effective quantity of the extract; and to aspalathin and rutin having anti-diabetic activity.

There is also provided a method for treating diabetes by administering to a human or animal an effective dosage of the said extract or the said composition.

According to a still further aspect, the invention also concerns the use of the said extract in the manufacture of a foodstuff or beverage to have an anti-diabetic effect when ingested.

The said foodstuff or beverage comprising an effective quantity of the said extract to have an anti-diabetic effect when ingested is also part of the present invention.

Preferably, the said extract comprises as an active ingredient aspalathin and/or a pharmaceutically acceptable salt or prodrug thereof.

According to a further aspect, the invention also concerns the said extract for use as a medicament having anti-diabetic activity.

The invention also extends to a pharmaceutical composition having anti-diabetic activity comprising an effective quantity of the said extract; and to aspalathin having anti-diabetic activity.

The active ingredient may be an extract from a plant of the genus *Aspalathus*, or a compound having the structure (aspalathin):

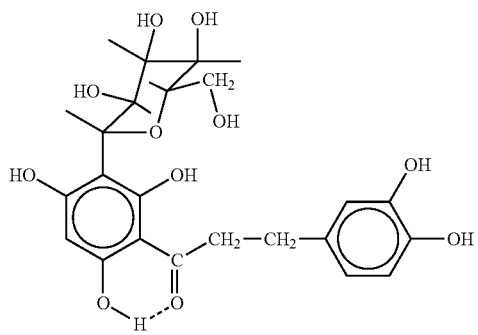

either extracted from a plant of the genus *Aspalathus* or prepared synthetically or a derivative thereof.

The plant may be of the species *Aspalathus linearis*.

Preferably, the compounds of the invention are prepared in pharmaceutically acceptable dosage forms. The anti-diabetic composition or formulation may consist of the anti-diabetic agent admixed with a pharmaceutical excipient, diluent or carrier. Other suitable additives, including a stabilizer and such other ingredients as may be desired may be added.

The composition may be prepared in unit dosage form.

As an anti-diabetic agent, aspalathin, or aspalathin in combination with rutin, is advantageously administered to a human in a dosage amount of from about 0.05 mg/kg/day to about 100 mg/kg/day. A preferred dosage range is about 0.1 mg/kg/day to about 50 mg/kg/day. When using the spray dried powder form of the extract of this invention, a preferred dosage range is about 0.5 mg/kg/day to about 100 mg/kg/day; especially preferred is about 1 mg/kg/day to about 50 mg/kg/day. Aspalathin and rutin is preferably in a molar ratio of 1:1 to 2:1.

According to a further aspect, the invention also concerns a pharmaceutical composition comprising an effective amount of:

i) an extract as mentioned above or aspalathin or aspalathin in combination with rutin, in association with ii) one or more other agents chosen from: representative agents to treat diabetes, glycogen phosphorylase inhibitors, sorbitol dehydrogenase inhibitors, glucosidase inhibitors, aldose reductase inhibitors.

Representative agents that can be used to treat diabetes include insulin and insulin analogs: (e.g., LysPro insulin, inhaled formulations comprising insulin); GLP-1 (7-37) (insulinotropin) and GLP-1 (7-36)-$NH_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; a2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; glitazones: ciglitazone, pioglitazone, englitazone, troglitazone, darglitazone, rosiglitazone; PPAR-gamma agonists; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; β-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; lipid-lowering agents: benfluorex, atorvastatin; antiobesity agents: fenfluramine, orlistat, sibutramine; vanadate and vanadium complexes (e.g., Naglivan®) and peroxovanadium complexes; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER1741 1, TER17529; gluconeogenesis inhibitors:GP3034; somatostatin analogs and antagonists; antipolytic agents: nicotinic acid, acipimox, WAG 994; glucose transport stimulating agents: BM-130795; glycogen phosphorylase inhibitors: glucose synthase kinase inhibitors: lithium chloride, CT98014, CT98023; galanin receptor agonists; MTP inhibitors such as those disclosed in U.S. provisional patent application No. 60/164,803; growth hormone secretagogues such as those disclosed in PCT publication numbers WO 97/24369 and WO 98/58947; NPY antagonists: PD-160170, BW-383, BW1229, CGP-71683A, NGD 95-1, L-152804; anorectic agents including 5-HT and 5-HT2C receptor antagonists and/or mimetics: dexfenfluramine, Prozac®, Zoloft®; CCK receptor agonists: SR-27897B; galanin receptor antagonists; MCR-4 antagonists: HP-228; leptin or mimetics:leptin; 11-beta-hydroxysteroid dehydrogenase type-I inhibitors; urocortin mimetics, CRF antagonists, and CRF binding proteins: RU-486, urocortin. Other anti-diabetic agents that can be used include ergoset and D-chiroinositol. Other anti-diabetic agents will be known to those skilled in the art.

Any glycogen phosphorylase inhibitor may be used as the second compound of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described hereinafter). A variety of these compounds are included in the following published PCT patent applications: PCT application publication WO 96/39384 and WO96/39385. However, other glycogen phosphorylase inhibitors will be known to those skilled in the art.

Any sorbitol dehydrogenase inhibitor may be used as the second compound of the invention. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

Any glucosidase inhibitor may be employed in combination with the extracts of this invention and with the aspalathin or aspalathin in combination with rutin, the stereoisomers and prodrugs thereof, and the pharmaceutically acceptable salts of the compounds, stereoisomers, and prodrugs; however, generally preferred glucosidase inhibitors comprise amylase inhibitors. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase inhibitors will be known to one of ordinary skill in the art. However, in the practice of the pharmaceutical compositions, combinations, methods, and kits of the instant invention, generally preferred glucosidase inhibitors are those inhibitors selected from the group consisting of acarbose, adiposine, voglibose, miglitol, emiglitate, MDL-25637, camiglibose, tendamistate, Al-3688, trestatin, pradimicin-Q and salbostatin.

The glucosidase inhibitor acarbose, O-4,6-dideoxy-4-[[(1S,4R,5S,6S)-4,5,6-trihydroxy-3-[(hydroxymethyl)-2-cyclohexen-1yl]-amino]-α-glucopyranosyl-(1→4)-O-α-D-glucopyranosyl-(1→4)-D-glucose, the various amino sugar derivatives related thereto and a process for the preparation thereof by the microbial cultivation of *Actinoplanes* strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., J. Antiobiotics, 35, 1234-1236 (1982). The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinertol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino]ethoxy]-benzota, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl)piperidino]β-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078.

The glucosidase inhibitor pradimicin-Q and a process for the preparation thereof by the microbial cultivation of *Actinomadura verrucospora* strains R103—3 or A10102, are disclosed in U.S. Pat. Nos. 5,091,418 and 5,217,877 respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Any aldose reductase inhibitor may be used in the pharmaceutical compositions, methods and kits of this invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, *Diabetes,* 29:861-864, 1980. "Red Cell Sorbitol, an Indicator of Diabetic Control"). The following patents and patent applications, each of which is hereby wholly incorporated herein by reference, exemplify aldose reductase inhibitors which can be used in the compositions, methods and kits of this invention, and refer to methods of preparing those aldose reductase inhibitors: U.S. Pat. No. 4,251,528; U.S. Pat. No. 4,600,724; U.S. Pat. No. 4,464,382, U.S. Pat. No. 4,791, 126, U.S. Pat. No. 4,831,045; U.S. Pat. Nos. 4,734,419; 4,883,800; U.S. Pat. No. 4,883,410; U.S. Pat. No. 4,883,410; U.S. Pat. No. 4,771,050; U.S. Pat. No. 5,252,572; U.S. Pat. No. 5,270,342; U.S. Pat. No. 5,430,060; U.S. Pat. No. 4,130, 714; U.S. Pat. No. 4,540,704; U.S. Pat. No. 4,438,272; U.S. Pat. No. 4,436,745, U.S. Pat. No. 4,438,272; U.S. Pat. No. 4,436,745, U.S. Pat. No. 4,438,272; U.S. Pat. No. 4,436,745, U.S. Pat. No. 4,438,272; U.S. Pat. No. 4,980,357; U.S. Pat. No. 5,066,659; U.S. Pat. No. 5,447,946; U.S. Pat. No. 5,037, 831.

A variety of aldose reductase inhibitors are specifically described and referenced below, however, other aldose reductase inhibitors will be known to those skilled in the art. Also, common chemical USAN names or other designations are in parentheses where applicable, together with reference to appropriate patent literature disclosing the compound.

Accordingly, examples of aldose reductase inhibitors useful in the compositions, methods and kits of this invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl}-N-methylglycine (tolrestat, U.S. Pat. No. 4,600, 724);
3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo-1(2H)-quinazolineacetic acid (zenarestat, U.S. Pat. No. 4,734,419, and U.S. Pat. No. 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl) methyl]-2H-1,4-benzothiazine-2acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);
10. (S)-6-fluorospiro[chroman-4,4'-imidazolidine]-2,50-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)-2',5'-dione (U.S. Pat. No. 4,438,272);
13. 2,7-di-fluoro-spiro(9H-fluorene-9,4'-imidazolidine)-2', 5'-dione (U.S. Pat. No. 4,436,745, U.S. Pat. No. 4,438,272);
14. 2,7-di-fluoro-5-methoxy-spiro(9H-fluorene-9,4'-imidazolidine)-2',5'-dione (U.S. Pat. No. 4,436,745, U.S. Pat. No. 4,438,272);
15. 7-fluoro-spiro(5H-indenol[1,2-b]pyridine-5,3'-pyrrolidine)-2,5'-dione (U.S. Pat. No. 4,436,745, U.S. Pat. No. 4,438,272);
16. d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357);
17. spiro[imidazolidine-4,5'(6H)-quinoline]-2,5-dione-3'-chloro-7',8'-dihydro-7',8'-dihydro-7'-methyl-(5-'-cis) (U.S. Pat. No. 5,066,659);
18. (2S,4S)-6-fluoro-2',5'-dioxospiro(chroman-4,4'-imidazolidine)-2-carboxamide (fidarestat, U.S. Pat. No. 5,447,946); and
19. 2-[(4-bromo-2-fluorophenyl)methyl]-6-fluorospiro[isoquinoline-4(1H), 3'-pyrrolidine]-1,2',3,5'(2H)-tetrone (minalrestat, U.S. Pat. No. 5,037,831).

The invention also extends to:
the use of the said association of the ingredients i) and ii) as mentioned above in the manufacture of a medicament having anti-diabetic activity;
the method of treating or preventing diabetes which comprises administering to a human or animal an effective dosage of the said association; and
kits or single packages combining the active ingredients (i) and (ii) as mentioned above, useful in treating or preventing diabetes.

The ingredients i) and ii) of the association can be administered simultaneously, separately, or sequentially in any order.

Preferably, the invention extends to a method of lowering or maintaining the glucose blood level by administering to a human or animal an effective dosage of an extract, or a compound as described above, or a composition containing the same.

Preferably, the invention extends to a method of lowering or maintaining the glucose blood level by ingesting a foodstuff or beverage containing an extract, or a compound as described above. More preferably, the invention also extends to the treatment of impaired glucose tolerance. Still more preferably, the invention provides a protective effect, in that the glucose blood level may not substantially increase after the arrest of the administration of an extract, compound, composition and/or foodstuff or beverage described above.

The present invention also provides a method for extracting the active ingredients from *Aspalathus linearis*.

The extract having anti-diabetic activity according to the invention may be prepared in accordance with the following process. The process for preparing an extract of a plant of the genus *Aspalathus* comprising a anti-diabetic agent includes the steps of treating collected plant material with a solvent to extract a fraction having anti-diabetic activity, separating the extraction solution from the rest of the plant material, removing the solvent from the extraction solution and recovering the extract. The extract so recovered may be further purified, e.g. by way of suitable solvent extraction procedures.

The extract may be prepared from plant material such as the leaves, stems and roots of said plants of the genus *Aspalathus*. In one application of the invention, the anti-diabetic extract is obtained from the species *Aspalathus linearis*.

The plant material may be homogenised in the presence of a suitable solvent, for example, a methanol/methylene chloride solvent, by means of a device such as a Waring blender. The extraction solution may then be separated from the residual plant material by an appropriate separation procedure such as, for example, filtration or centrifugation. The solvent may be removed by means of a rotary evaporator, preferably in a water bath at a temperature of 60° C.

The separated crude extract may then be further extracted with methylene chloride and water before being separated into a methylene chloride extract and a water extract. The methylene chloride extract may have the solvent removed preferably by means of evaporation on a rotary evaporator and the resultant extract may be further purified by way of a methanol/hexane extraction. The methanol/hexane extraction product may then be separated to yield a methanol extract and a hexane extract. The methanol extract may be evaporated to remove the solvent in order to yield a partially purified active extract.

The partially purified active extract may be dissolved in methanol, and may be further fractionated by column chromatography, employing silica gel as an adsorption medium and a chloroform/30% methanol mixture as an eluent. A plurality of different fractions may be obtained, and each may be evaluated, by suitable bioassaying procedures, to determine the anti-diabetic activity thereof.

A fraction having anti-diabetic activity may preferably be further fractionated such as by column chromatography using silica gel as an adsorption medium and a 9:1 chloroform:methanol solvent, and the resultant sub-fractions bioassayed for their anti-diabetic activity. A sub-fraction displaying anti-diabetic activity may, if desired, be further fractionated and purified, conveniently using a column chromatographic procedure with silica gel as the adsorption medium and a 9:1 ethylacetate:hexane solvent. The resultant purified fractions may again be evaluated by suitable bioassay procedures for their anti-diabetic activity.

The inventors have found that at least one such purified fraction has good anti-diabetic activity, and the active principle in the fraction was identified by conventional chemical techniques including nuclear magnetic resonance, and was found to be aspalathin.

The extract may be dried to remove moisture, e.g. by spray-drying, freeze-drying or vacuum drying, to form a free-flowing powder.

The invention and its efficacy is further described, without limitation of the scope of the invention with the following examples and drawings.

EXPERIMENTAL

Experiment I

Plant Extract (Laboratory Scale)

Green plant material refers to plant material that is dried in such a manner to prevent enzymatic/chemical oxidation of the plant polyphenols and in particular the flavonoids. Different drying procedures can be used.

Oxidised plant material refers to plant material that is oxidised for several hours after cutting of leaves and stems. The latter process initiates enzymatic and chemical oxidation of the polyphenols, in particular the flavonoids. A water/enzyme (s) mixture can be added to aid enzymatic/chemical changes that takes place during the oxidation step of processing.

In the below examples the plant extract used have been obtained by the following procedure.

The preparation procedure involved steeping 100 g of milled plant material/*Aspalathus* linearis leaves (1 mm sieve) in 1000 mL freshly boiled deionised water for 5 minutes. Extracts were then coarse filtered with a Buchner filter, using a 125 µm synthetic mesh cloth (Polymer PES D25/35 supplied by Swiss Silk Bolting Cloth Mfg. Co. Ltd, Zurich, Switzerland), followed by filtration with Whatman No. 4 filter paper (Whatman International Ltd., Maidstone, England) to remove finer particles. The filtrates were freeze-dried in an Atlas pilot-scale freeze-drier (Denmark model, Copenhagen, Denmark, 40° C. shelf temperature) after being frozen at −20° C. in plastic trays (170×115×30 mm). The freeze-dried aqueous extracts were placed in clear glass vials and stored in desiccators under vacuum in the dark.

1. Tissue Culture: In Vitro Assay Models (Cell Lines) for Anti Diabetic Screening Diabetes is a multi factorial disease that affects many organs differently. Therefore, a combination of three cell lines, each representing a different organ affected by diabetes, plus a unique but simple, non-radioactive method, are used to measure glucose utilization, instead of glucose transport, Method The method measures the utilisation of glucose by 3T3-L1 adipocytes, Chang liver cells and C2C12 myocytes in 96-well plates, over a period of one to three hours, depending on the cell line. This is done by starving the cells, adding glucose and then monitoring the disappearance of glucose from the incubation medium in the presence and absence of test samples. The adipocytes and liver cells are pre-exposed to the test samples for 48 hours, prior to the measurement of glucose utilization, to ensure that any chronic effects are also considered. Viability of cells exposed to the extracts for 48 hours is compared to that of control cells, allowing the identification of potentially toxic samples. Longer incubation times, and measurement of glucose utilisation or metabolism, allows detection of alterations in any of the pathways that are involved in glucose metabolism, not only in glucose transport. Table 1 summarises the responses measured in the three cell lines. This combination covers the mechanism of action of all classes of hypoglycaemic drugs currently available for the treatment of type 2 diabetes, except those that reduce intestinal glucose absorption.

TABLE 1

Summary of the three cell lines used for routine anti diabetic screening

| CELL LINE | RESPONSE MEASURED | GLUCOSE TRANS-PORTER | ACUTE/CHRONIC EFFECTS MEASURED | ACTION SIMILAR TO |
|---|---|---|---|---|
| 3T3-L1 fat cell | Glucose utilisation | GLUT4 (insulin responsive) | Chronic | Thiazolidine-diones Insulin |
| Chang liver | Glucose utilisation | GLUT2 (not insulin responsive) | Chronic | Biguanides |
| C2C12 muscle | Glucose utilisation | GLUT4 | Acute | Insulin |

The extracts of the present invention were found to be effective in increasing glucose uptake in the C2C12 cell line, displaying activity similar to insulin. The extracts were effective in the CHANG liver cells, displaying activity similar to Biguanides 2. Streptozotocin Model (T1 D) or Late Stage T2D Adult male Wistar rats (200-250 g) were used throughout the studies. Adult male Wistar rats were injected intra muscularly with streptozotocin (STZ), at a dose of 36 mg/kg, to reduce or deplete their insulin producing cell numbers and induce hyperglycaemia at levels typical of type 1 diabetes or late stage T2D. Rats were fasted for 3 hours but were given drinking water ad libitum. At 72 hours after STZ injection, blood samples were taken from the tail vein. Plasma glucose concentrations were determined by using a glucometer (Precision Q.I.D.; Abbott Laboratories) using the glucose oxidase method. Rats with a blood glucose level of more than 300% of the fasting level were considered diabetic and were selected for the studies.

Acute Effect of the Extract on Plasma Glucose in STZ Rats

Diabetic rats were divided into 4 groups, each containing six rats.

Gavage Procedure:

Diabetic rats were injected intraperitoneally with 20 mg/kg sodium pentobarbital to induce a lightly anaesthetized state. Approximately 10 to 15 minutes later, the rats was sufficiently calm to allow easy and stress-free handling, but with swallow-reflex intact. A Teflon gavage catheter was placed into the stomach via the mouth and esophagus, and 1 ml of water, containing the required extract, was injected directly into the stomach. An additional volume of approximately 200 ul of water was then injected to flush any remaining extract from the gavage catheter. The catheter was then promptly removed and the rat placed in its cage for recovery. Group A was given normal saline, group B was given 5 mg/kg of the plant extract, group C was given 25 mg/kg of the plant extract and group D was given 50 mg/kg of the plant extract. Plasma glucose was measured at 1 hr intervals for 6 hours.

Oral Glucose Tolerance Test (OGTT)

Diabetic STZ rats, fasted for 16 hours received 25 mg/kg plant extract per gavage under light anesthesia (fluothane). After three hours the animals received an oral glucose bolus of 1 g/kg. Plasma glucose levels in mmol/l were determined at 0, 1, 5, 10, 15, 20, 30, 60 and 120 minutes.

In adult male Wistar rats, injected with streptozotocin to reduce or deplete B-cells, an acute oral administration of the extract elicited a progressive reduction in plasma glucose over a 6 hr period. At the lowest dose of 5 mg/kg, the plant extract reduced plasma glucose by 16% after 1 hr, increasing to 31% after 6 hr.

Figure 3:
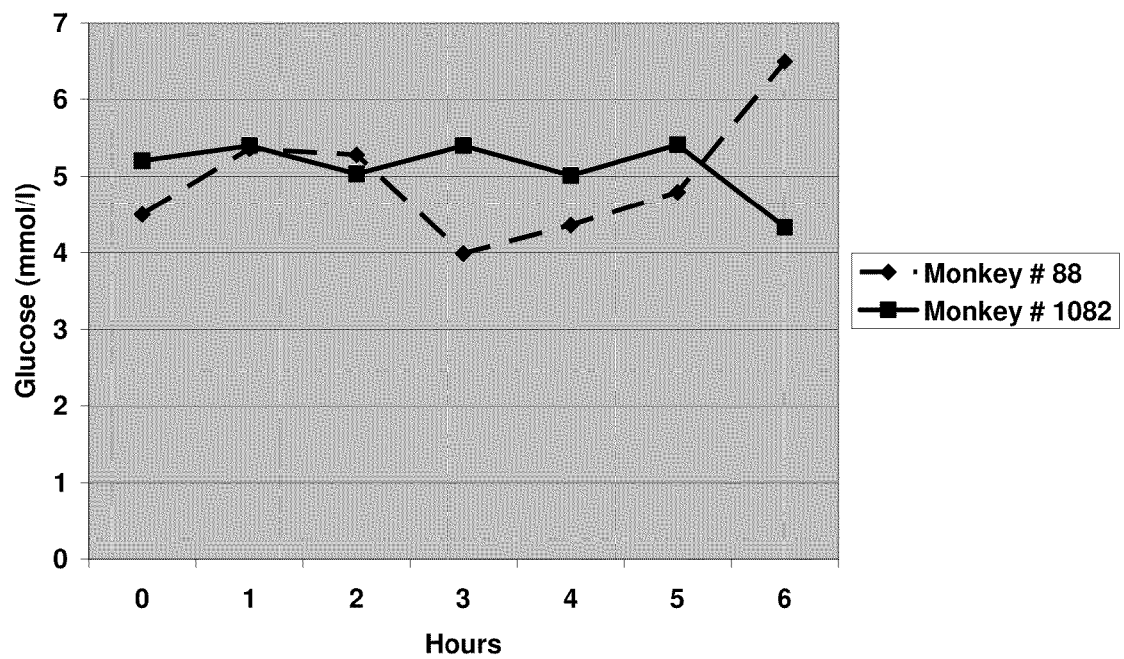
FIG. 3. Shows hourly blood glucose values of the two control monkeys plotted over a 6 hour monitoring period. The baseline values (0 hours) represent the fasting blood glucose values before the maintenance diet bolus was fed to the monkeys.
Figure 4:
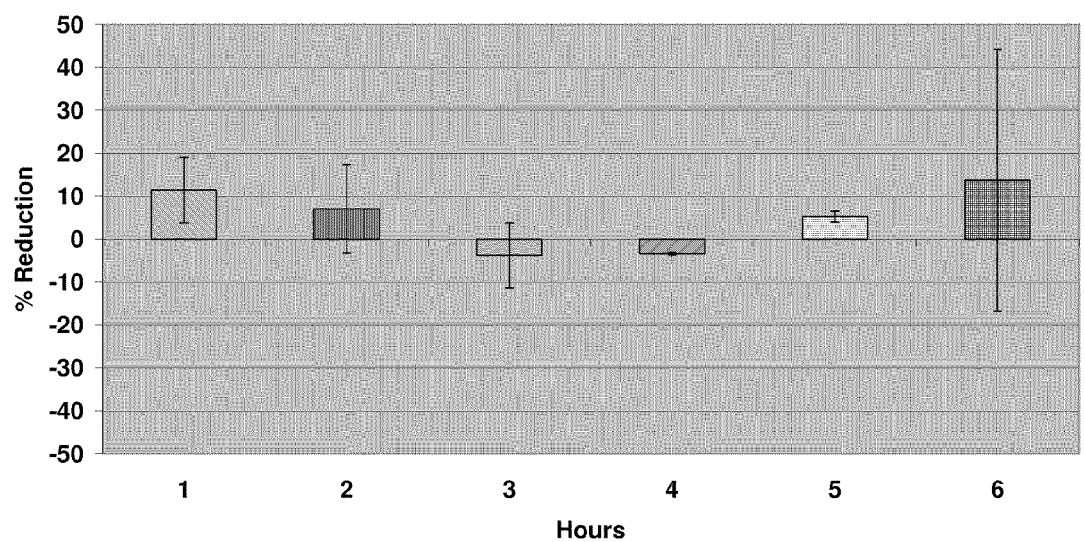
FIG. 4. Shows the mean percentage blood glucose decline or increase as calculated from the baseline blood glucose level in the control group. Blood glucose values were maintained around the baseline values with slightly lower values seen at three, four and five hours after the monkeys received a 70 g maintenance diet portion.
Figure 5:
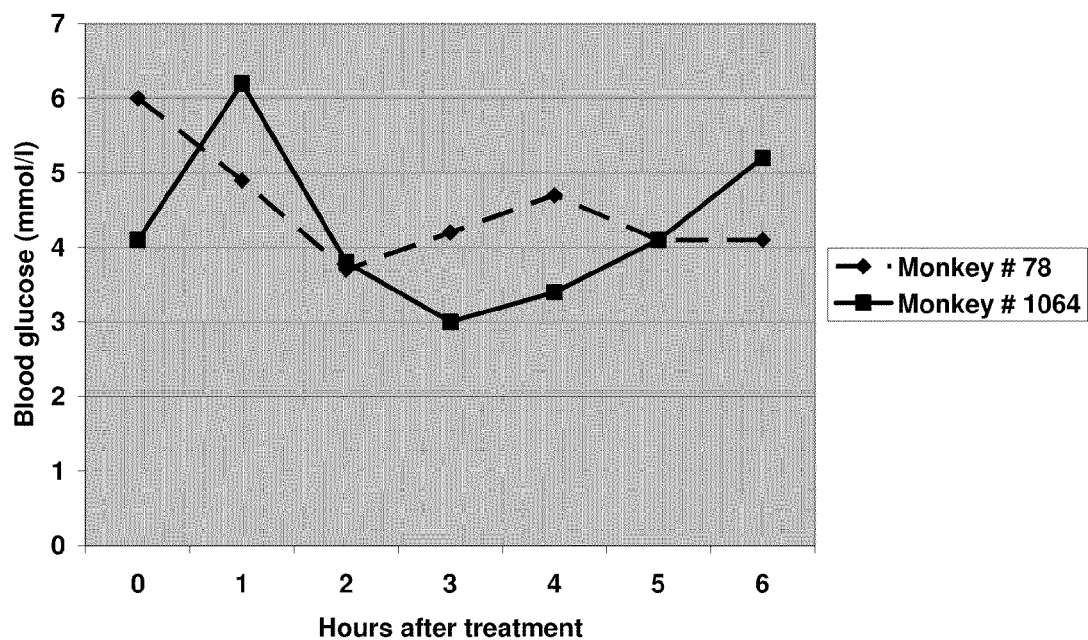
FIG. 5. Shows blood glucose values of the two monkeys in the experimental group receiving 1.0 mg/kg GMP ARC61 plotted over a 6 hour monitoring period. The baseline values (0 hours) represent the fasting blood glucose values before the maintenance diet bolus containing 1.0 mg/kg GMP ARC61 was given to the monkeys.
Figure 6:
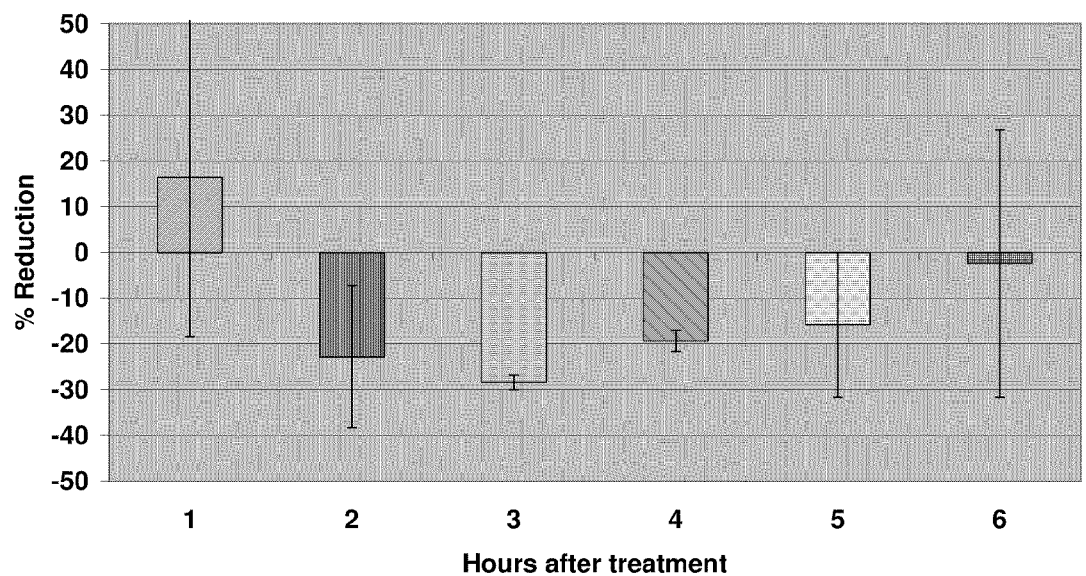
FIG. 6. Shows the mean percentage blood glucose decline or increase as calculated from the baseline blood glucose level. The highest percentage reduction of blood glucose occurred at 3 hours after receiving 1.0 mg/kg GMP ARC61. Marked lower glucose levels were still maintained over a 5 hour period.
Figure 7:
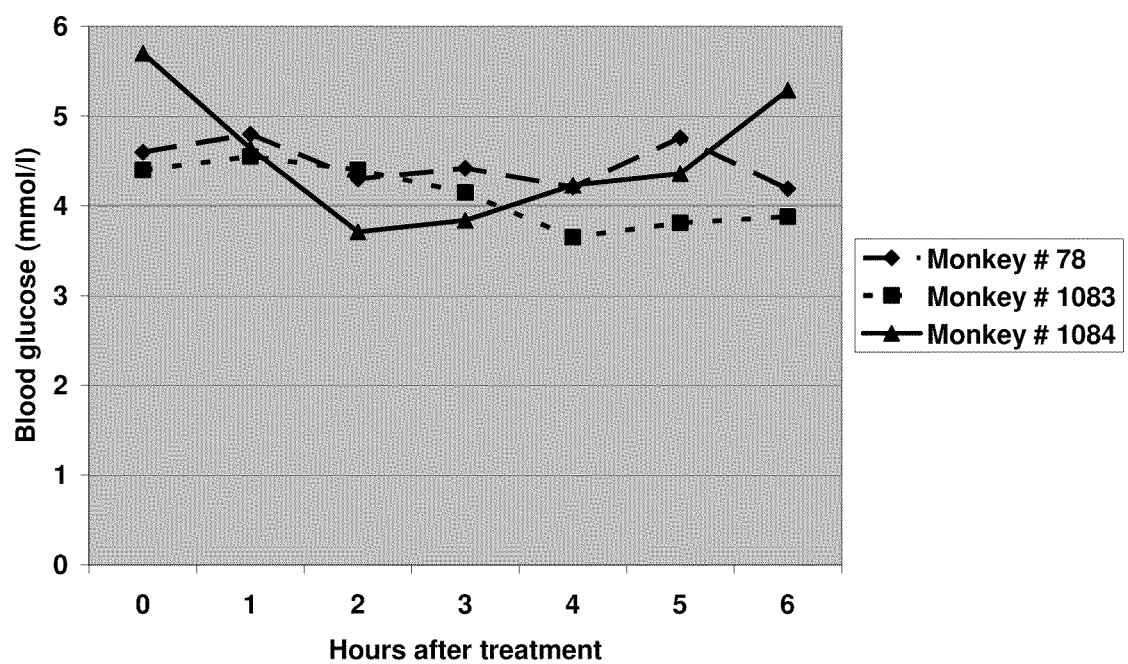
FIG. 7. Shows blood glucose values of the three monkeys in the experimental group receiving 2.5 mg/kg GMP ARC61 plotted over a 6 hour monitoring period. The baseline values (0 hours) represent the fasting blood glucose values before the maintenance diet bolus containing 2.5 mg/kg GMP ARC61 was given to the monkeys FIG. 8. Shows the mean percentage blood glucose decline or increase as calculated from the baseline blood glucose level. The highest percentage reduction of blood glucose occurred at 2 hours after receiving 2.5 mg/kg GMP ARC61. Marked lower glucose levels were still maintained for the 6 hour period.
Figure 8:
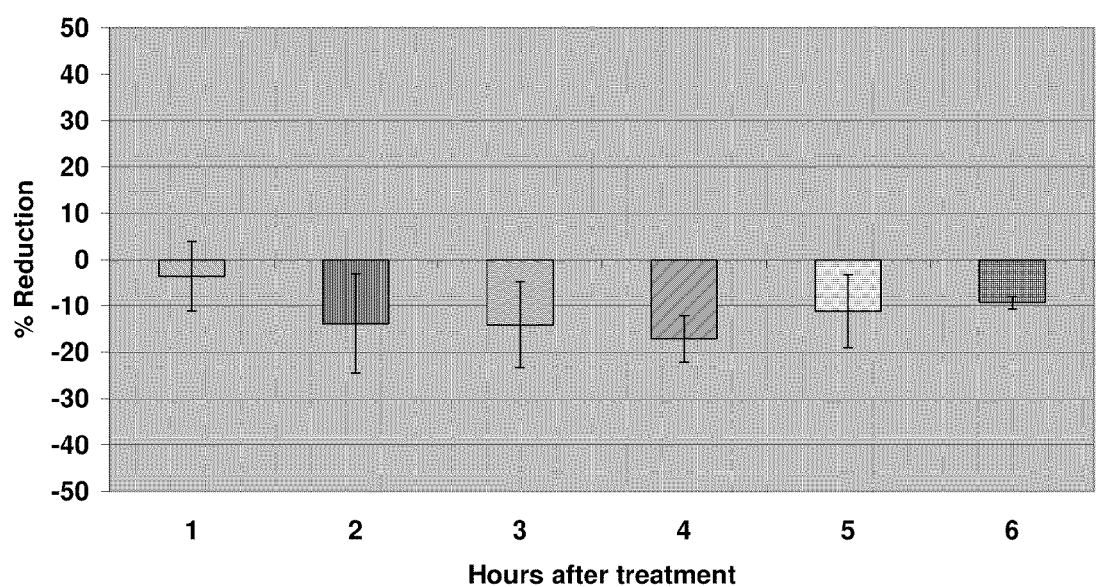
Figure 9:
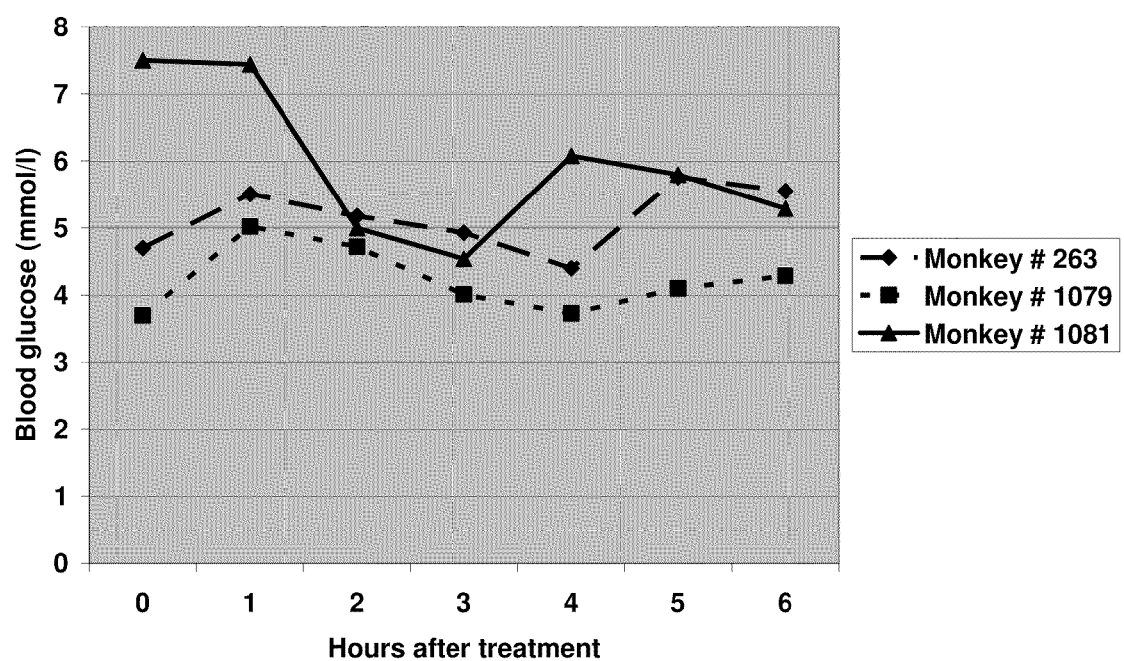
FIG. 9. Shows blood glucose values of the three monkeys in the experimental group receiving 5 mg/kg GMP ARC61 plotted over a 6 hour monitoring period. The baseline values (0 hours) represent the fasting blood glucose values before the maintenance diet bolus containing 5.0 mg/kg GMP ARC61 was given to the monkeys.
Figure 10:
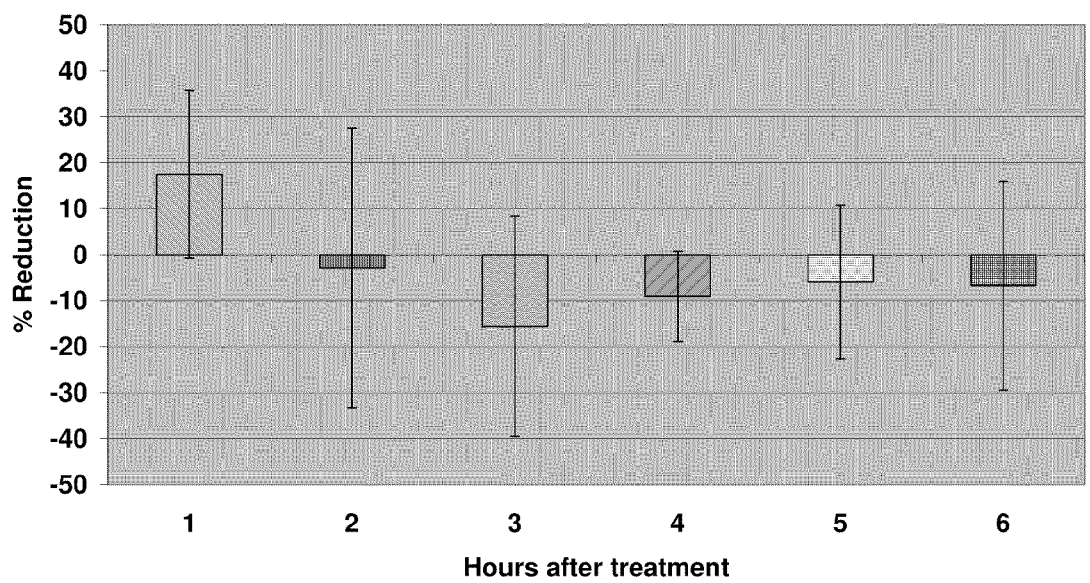
FIG. 10. Shows the mean percentage blood glucose decline or increase as calculated from the baseline blood glucose level. The highest percentage reduction of blood glucose occurred at 3 hours after receiving 5 mg/kg GMP ARC61. Lower glucose levels were still maintained for the rest of the monitoring period.
Figure 11:
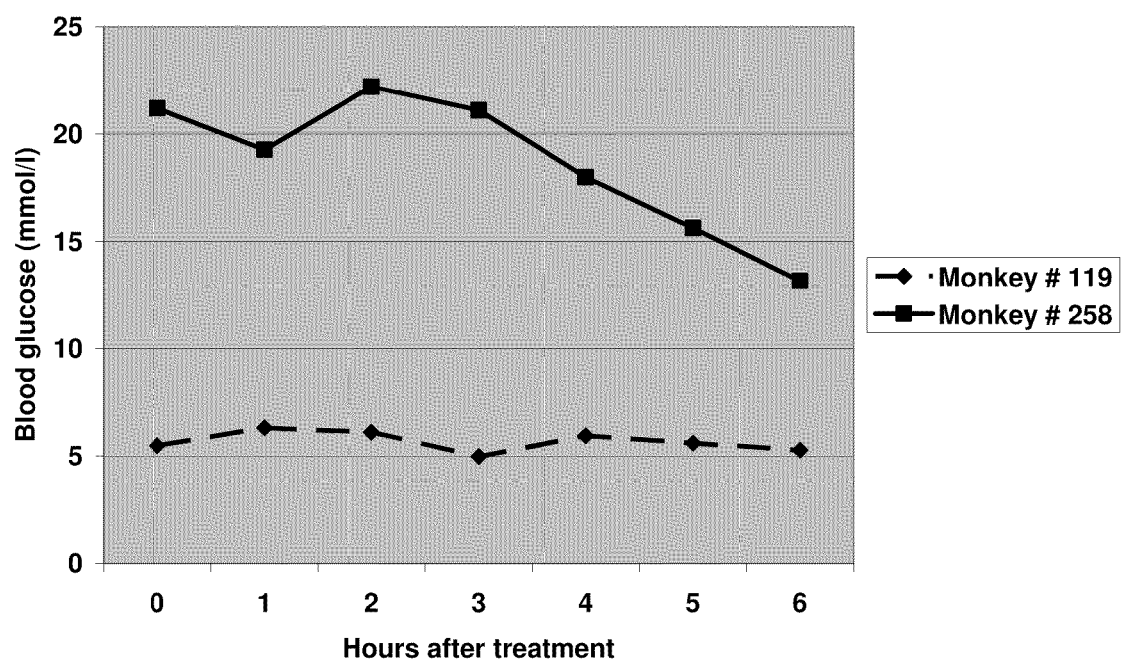
FIG. 11. Shows blood glucose values of the two monkeys in the experimental group receiving 25 mg/kg GMP ARC61 plotted over a 6 hour monitoring period. The baseline values (0 hours) represent the fasting blood glucose values before the maintenance diet bolus containing 25 mg/kg GMP ARC61 was given to the monkeys.
Figure 12:
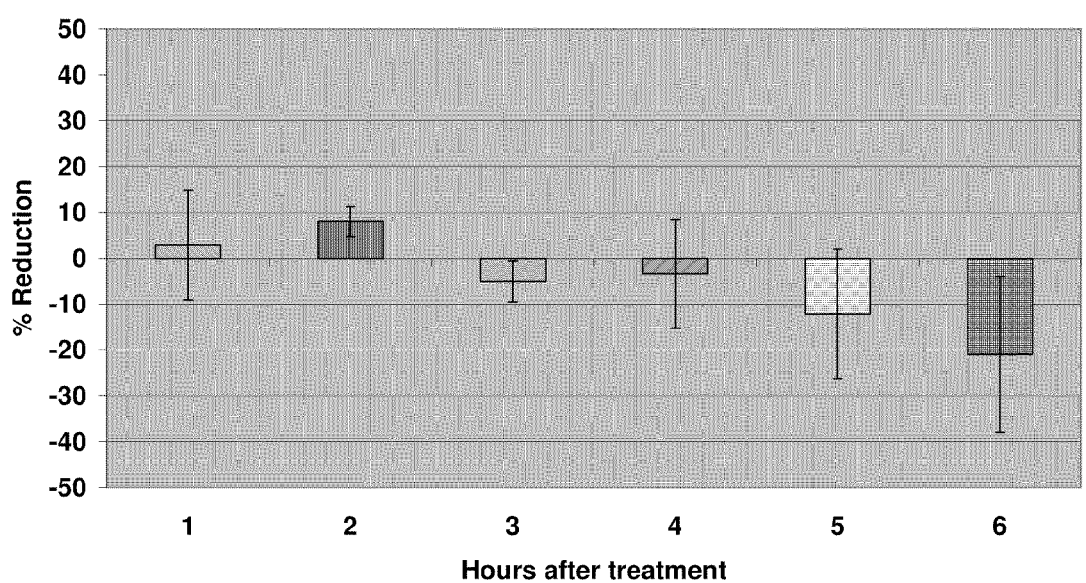
FIG. 12. Shows the mean percentage blood glucose decline or increase as calculated from the baseline blood glucose level. After receiving the 25 mg/kg GMP ARC61 blood glucose percentages were marginally lower than the baseline levels from 3 hours with the highest percentage reduction of blood glucose percentage occurring at 5 and 6 hours.
Figure 13:
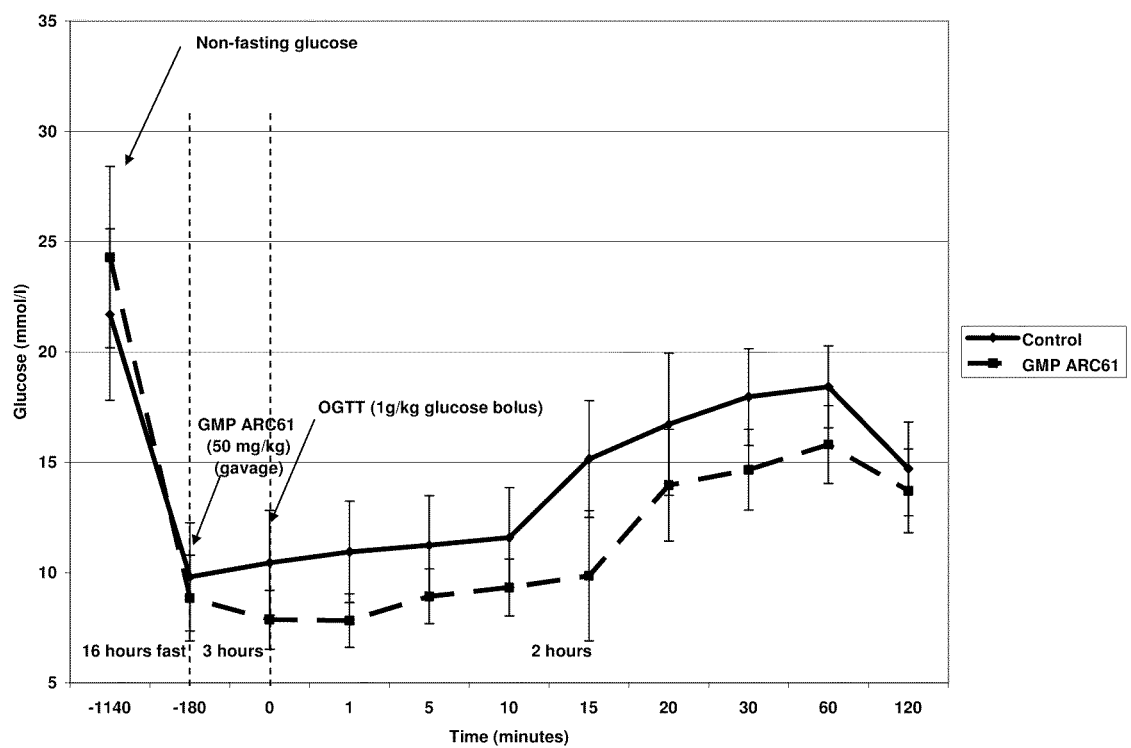
FIG. 13. Shows the results of the OGTT (1 g/kg glucose) performed three hours after a single 50 mg/kg GMP ARC61 oral dose. The resulting plasma glucose levels of the STZ rats were lower when compared to control glucose values at all the time points taken.
Figure 14:
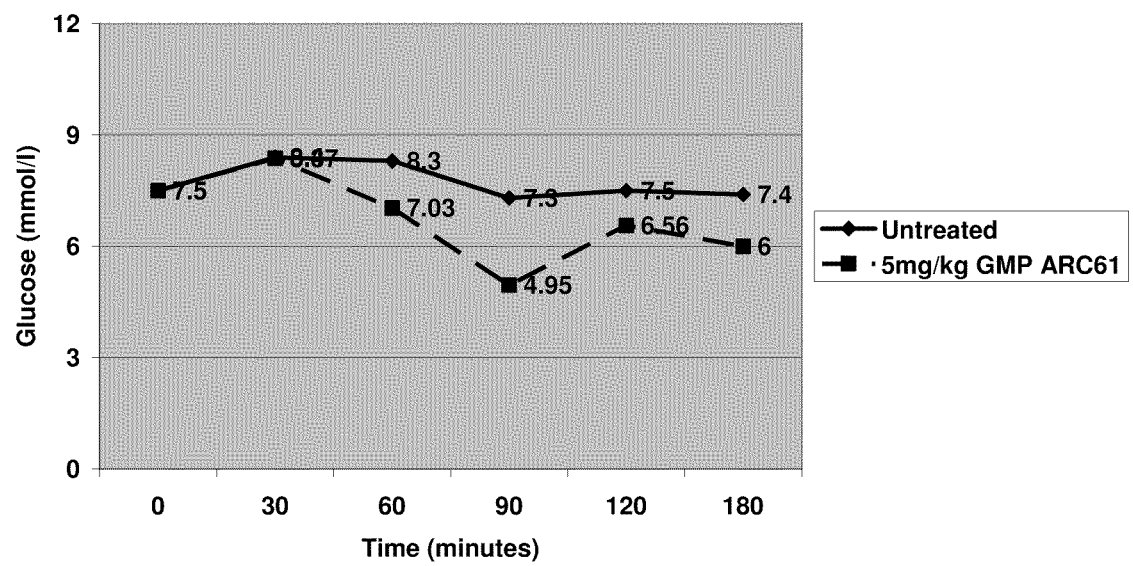
FIG. 14. Shows the results of the OGTT (1.75 g/kg glucose) performed over three hours after a single 5 mg/kg GMP ARC61 oral dose. The resulting plasma glucose levels of monkey #1081 were lower at all time points when compared to untreated monkey glucose values after the initial 30 minutes.

Results of the OGTT (1 g/kg glucose) performed three hours after a single 25 mg/kg oral dose of the plant extract showed that the plasma glucose levels of the STZ rats were lower when compared to control glucose values at all the time points taken (see FIG. 3).

3. Wistar Rat Skeletal Muscle Model: 2-Deoxyglucose Uptake

Adult lean male Wistar rats (200-250 g) were used throughout the studies. Lean rats were divided into 7 groups, of each containing six rats.

Gavage Procedure:

Lean rats were injected intraperitoneally with 20 mg/kg sodium pentobarbital to induce a lightly anaesthetized state. Approximately 10 to 15 minutes later, the rats was sufficiently calm to allow easy and stress-free handling, but with swallow-reflex intact. The rats were injected via their tail vein with 50% glucose at a dose of 0.5 mg/kg over a 20 second period. A Teflon gavage catheter was placed into the stomach via the mouth and esophagus and 1 ml of water, containing the required extract, was injected directly into the stomach. An additional volume of approximately 200 ul of water was then injected to flush any remaining extract from the gavage catheter. The catheter was then promptly removed and the rat placed in its cage for recovery. Group A was given water, group B was given 2.5 mg/kg of the plant extract, group C was given 5 mg/kg of the plant extract, group D was given 12.5 mg/kg of the plant extract, group E was given 25 mg/kg of the plant extract, group F was given 50 mg/kg of the plant extract and group G was given 300 mg/kg of the plant extract. After 1 hour the animals were euthanased and skeletal muscle was collected and snap frozen in liquid nitrogen.

The best results for glucose uptake in lean rat skeletal muscle were obtained with 5 mg/kg and 50 mg/kg.

Overall Result

Fasting glucose levels were significantly reduced in streptotocin treated rats, treated with the extract of the present invention.

CONCLUSIONS

Similar efficacy to Thiazolidines and insulin (in fat cell studies) and Biguanides (in Chang liver cells) in increased glucose uptake has been demonstrated with Plant 2 extract.

Treatment with the extract was effective in reducing plasma glucose levels in streptozotocin treated (late stage T2D).

The extract displays encouraging efficacy in normalizing compromised glucose levels.

Experiment II

The present experiment elucidates the optimal dose of the plant extract according to the present invention for reducing plasma glucose levels. In this experiment monkeys were used in order to resemble the situation of a human as closely as possible.

Justification and Validation for Use

The Vervet monkey (*Chlorocebus aethiops*), also called African Green monkey, is one of two African nonhuman primate species, most commonly utilized in biomedical research and endemic to Southern Africa. With some exceptions, the use of nonhuman primates internationally has been influenced more by geopolitical and logistical rather than biological considerations. The vervet monkey is taxonomically closely related to the macaques (i.e. rhesus), since all belong to the same subfamily (Fairbanks 2002).

Although vervet monkeys are used in many fields including virology, bacteriology, parasitology, neurology, toxicology, reproduction and cell biology, they have proven to be particularly useful in the areas of cardiovascular and metabolic disease. As a result, the literature abounds with information and data, validating this well established model (de Vries et al. 2007, Fairbanks 2002, Fincham et al. 1998, Kavanagh et al. 2007, Louw et al. 1997, Martin et al. 1990, Rudel et al. 1981, Smuts et al. 1992, Suckling and Jackson 1993, Wallace et al. 2005, Weight et al. 1988).

It is important to stress that vervet monkeys develop spontaneous obesity, insulin resistance and type 2 diabetes (Fairbanks 2002, Francis et al. 1999, Kavannagh et al. 2007, Tigno et al. 2005). As much as 25% females and 16% males of a particular colony have been reported to be obese (Kavannagh et al. 2007). As humans, non human primates develop all the associated complications including renal, vascular and neurological (Tigno et al. 2005). In some vervet monkey populations as much as 4% can have abnormally high plasma glucose concentrations (Fairbanks 2002, Kavanagh et al. 2007), and there is a strong positive association between waist circumference, increased plasma insulin as well as plasma triglyceride concentrations (Kavannagh et al. 2007). It has also been established that obesity and associated plasma lipids and other risk factors are heritable in this species (Kavannagh et al. 2007).

It is also important to note that vervet monkeys develop spontanous atherosclerosis and respond well to experimental nutritional manipulations to produce dyslipidaemia and ultimately atherosclerosis (Fairbanks 2002, Rudel et al. 1981, Fincham et al. 1998, Suckling and Jackson 1993). The associated underlying mechanisms and lesions model the human condition (Fincham et al. 1996, Fincham et al. 1998, Rudel et al. 1981), and vervet monkeys are responsive to well recorded older and more novel pharmacological intervention strategies (Fincham et al. 1996, St. Clair et al. 1981, Wallace et al. 2005).

Primate Management

In the present study primate management and care was according to the documented Standard Operating Procedures (Mdhluli 2005) and the MRC Guidelines on the Use of Animals in Research and Training, the National Code for Animal Use in Research, Education, Diagnosis and Testing of Drugs and related Substances in South Africa, and the Veterinary and Para-Veterinary Professions Act of 1997: Rules relating to the practicing of the Para-Veterinary Profession of Laboratory Animal Technologist.

Choice of Monkeys and their Permanent Identification

All individuals selected for this study were healthy adult males and females, 2nd generation captive bred, with an average weight of 5.56 kg (±0.724) and 3.16 kg (±0.266) respectively. Average age was 12 years for males and 7 years for females. Female vervet monkeys mature sexually in captivity at about 2.5 to 3.0 years of age, and males at about 3.0 to 4.0 years (Eley 1992).

All individuals were free of overt pathology as judged by physical examination and previous clinical record, of normal weight for age, and identified with a permanent number in ink tattoo. Additionally, cages were marked according to individual number, group designation, and experiment number.

Environmental Conditions

All vervet monkeys used in this study were maintained in the Primate Unit of the Technology and Innovation directorate of the MRC under identical housing conditions. The facility consists of 14 fully air conditioned animal rooms in a closed indoor environment that is maintained at 24-26° C., a humidity of about 45%, about 15-20 air changes per hour and a photoperiod of 12 hours. All rooms are kept under positive pressure and have separate air supply.

Housing

Caging was singly for the duration of the study, and consisted of 90×70×120 cm suspended galvanized steel cages, with 24 monkeys being maintained in one room. Animal rooms were sanitized once daily. The cage size is consistent with the requirements of the South African National Code for single animals.

Food and Water

Water was available ad lib via an automatic watering device. The maize meal based maintenance diet was produced in the Primate Unit, and has supported good growth and reproduction for three generations (Seier 1986). Seventy gram of the dry maize meal, which contains added micro- and macronutrients, was mixed with water to a stiff consistency and fed to the monkeys at 7:00 am, 11:00 am and another 70 g at 3:00 pm but without the added nutrients. This supplies 2412 kJ per monkey per day with 12% energy from protein, 20% from fat and 68% from carbohydrates. In addition, apples or oranges are fed at noon at 70 g/monkey/day. The detailed composition of the diet has been described previously (Fincham et al. 1987, Venter et al. 1993).

Supporting Facilities

All activities of the Primate Unit are fully physically separated by dedicated areas and rooms for cage sanitation, food preparation and storage, storage and formulation of compounds under investigation, procedures (i.e. blood sampling), operations (theatre) and necropsy.

Environmental Enrichment

Single cages are fitted with resting perches, 80 cm above the cage floor, foraging pans and communication panels, which enable grooming and physical contact with conspecifics. Exercise cages measuring 90×70×200 cm area available three times/week to each monkey and enable leaving the home cages and engaging in certain activities that are not possible in home cage (Seier and de Lange 1996). The cage also enables 360° communication with all other animals in the room as well as the adjacent room (through glass panels). Soft music and bird sounds are broadcasted into each animal room to relieve auditory monotony. Other enrichment methods have been described previously (Seier et al. 2004).

Health and Disease Control

All animals were tested for TB four times per year by injecting 3000 units of PPD intradermally into the upper eyelid. MRC staff and students, as well as service providers, were tested for TB twice per year by culturing bronchial secretions for *Mycobacteria*. According to Primate Unit SOPs, additional bacteriological and serological testing is carried out on the vervet monkeys from time to time, and is consistent with accepted standards (FELASA 1998). This includes testing for *Shigella, Salmonella, Campylobacter* and *Yersinia*.

Handling of Vervet Monkeys, Administration of Substance, and Collection of Samples Procedures and handling of the vervet monkeys were according to Primate Unit SOPs, and all other guidelines mentioned in the preamble. They are carried out and/or supervised by fully qualified and experienced laboratory animal technologists who are registered with the SA Veterinary Council in laboratory animal technology.

Observations

All animals have been observed three times/day to determine potential physical side effects of the treatment. The following criteria were used: posture, coordination, locomotion, activity, behaviour (alert, fearful, aggressive, confused, depressed, vocalization), discharge from orifices, appetite, condition of feces and urine.

Preparations of GMP ARC61

Preparation of a plant extract in accordance with the present invention was made for testing of bio-activity in the primate model. "Fermented" *Aspalathus linearis* leaves and stems, pretested for the bio-activity, was processed in a cGMP facility.

Manufacturing Details

The manufacturing process for both products comprised the following unit operations: extraction of the plant material, separation of the extract and small particulate matter, evaporation, HTST sterilization of the concentrate, vacuum drying of the concentrate and sieving of the final product powder.

Preparation of Extract

The plant material (*Aspalathus linearis* leaves and stems) was extracted in two subsets of 300 kg per percolator. Purified water (3000 kg), preheated to 93° C. was introduced into the percolator from the top at a rate of 1:10 and the resulting extract was circulated for 35 min. At completion of extraction sub set 1 was drained to give a total of 2445 kg of aqueous extract with a dry residue of 1.24% (dry extract yield— 10.1%). Sub set 2 was extracted in a similar manner, but after draining an additional 300 kg of purified water was flushed through the extracted plant material to give 2771 kg aqueous extract with a dry residue of 1.25% (dry extract yield— 11.6%).

The extract was centrifuged warm at a flow rate of 700 l/h, with a draining cycle of the sediment every 30 min. The final extract recovered after centrifugation was 5130 kg with a dry residue yield of 1.24%.

After centrifugation the aqueous extract an inlet temperature of between <78° C. was concentrated with a plate evaporator under vacuum at <55° C. to 310 kg and a dry residue of 21.95%.

The concentrate was HTST sterilized at 121-123° C. (ca 68 s) at a flow rate of 385-445 l/h. The concentrate was cooled to <25° C. after sterilization. Purified water was used to wash out the plant, giving a final sterilized concentrate of 322 kg with a dry residue of 20%.

The sterilized concentrate was dried in a vacuum drier (Model 2000) at a product temperature <35° C. for 36 h and then 48° C. for 24 h. After drying the power was sieved through two sieves (2 mm followed by 0.5 mm) to remove lumps that formed during the rotation of the paddles in the vacuum drier.

The sieved powder was placed in one PE bag (51.2 kg), which were then sealed in an aluminium coated fibre drum.

Plant Material

The HPLC fingerprint of the plant material was determined on an aqueous extract in accordance with the present invention. The extract was prepared by extracting the plant material with deionised, purified water at 90-93° C. (giving 1:10 ratio) for 30 min in a water bath, filtering warm through Whatman no. 4 filter paper and frozen, whereafter it was freeze-dried. For HPLC analysis the freeze-dried extract was reconstituted in purified water.

Results

The HPLC fingerprint of the plant material was determined on an aqueous extract in accordance with the present invention. The extract was prepared by extracting the plant material with deionised, purified water at 90-93° C. (giving 1:10 ratio) for 30 min in a water bath, filtering warm through Whatman no. 4 filter paper and frozen, whereafter it was freeze-dried. For HPLC analysis the freeze-dried extract was reconstituted in purified water.

The HPLC fingerprint of the final product (GMP ARC61) was determined on the extract reconstituted in purified water.

Vervet Monkey Dose Optimization Study

Controls

Three monkeys where randomized into a control group. The monkeys in the control group received a 70 g ration of maintenance diet (molded into ball) but without the dry extract, three times a day for 7 days. On day 7 the monkeys were fasted overnight (13 hours), a baseline blood sample was collected before the monkeys were fed the ball maintenance diet bolus. Thereafter blood samples were collected hourly for a six hour period by femoral venipuncture under Ketamine anaesthesia (10 mg/kg bodyweight intramuscular injection).

Experimental Groups

Three monkeys randomized into four experimental groups receiving 0.1 mg/kg, 0.3 mg/kg, 1 mg/kg, 2.5 mg/kg, 5 mg/kg and 25 mg/kg GMP ARC 61 (extract of *Aspalathus linearis* leaves and stems as described above) three times a day. All the monkeys in the respective experimental groups received a pre-weighed aliquot of plant extract moulded into a 70 g ball of maintenance diet as a bolus, three times a day for 7 days. On day 7 after the monkeys were fasted overnight (13 hours), a baseline blood sample was collected before the monkeys were fed the maintenance diet bolus containing the respective amounts of dry extract. Thereafter blood samples were collected hourly for a six hour period by femoral venipuncture under Ketamine anaesthesia (10 mg/kg bodyweight intramuscular injection).

Summary of Results

Control Group

In the control group none of the three monkeys tested showed a decline from the baseline values during the first two hours after receiving the portion of moulded maintenance diet. Thereafter in two of the three monkeys there was a reduction of the glucose values when compared to their baseline values.

Blood Glucose Values in the 1.0 Mg/Kg GMP ARC61 Treatment Group.

Results of the 1 mg/kg GMP ARC61 groups showed a marked reduction in the blood glucose values compared to the baseline blood glucose levels in two monkeys, for the whole six hour monitoring period.

Blood Glucose Values in the 2.5 Mg/Kg GMP ARC61 Treatment Group.

The blood glucose levels of the three monkeys receiving 2.5 mg/kg GMP ARC61 showed a marked reduction in their blood glucose levels over the first two hours and thereafter the lower blood glucose levels were maintained for the rest of the monitoring period.

Blood Glucose Values in the 5 Mg/Kg GMP ARC61 Treatment Group.

The monkeys showed a marked reduction of blood glucose levels from two hours after receiving the 5 mg/kg GMP ARC61. These levels were maintained for the duration of the monitoring period.

Blood Glucose Values in the 25 Mg/Kg GMP ARC61 Treatment Group.

The monkeys largely failed to respond to the treatment at the given dose.

Figure 15:
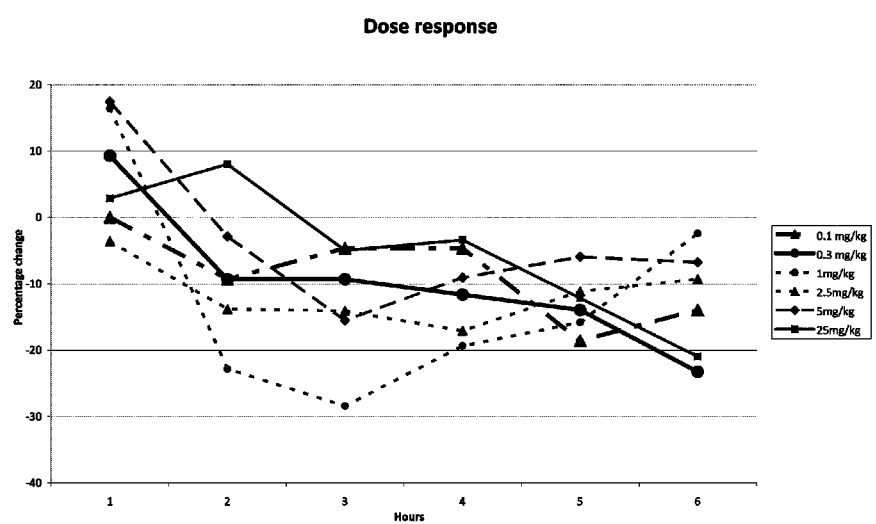
FIG. 15. Shows % reduction in plasma glucose over a 6 hour period following treatment with different dosages of the extract (GMP ARC61) for 7 days in Vervet monkey.

FIG. 15 shows % reduction in plasma glucose over a 6 hour period following treatment with different dosages of the extract (ARC61) for 7 days in the Vervet monkey (average data).

CONCLUSION

In the small pilot study, GMP ARC61 in the dose range of 1-2.5 mg/kg was the most effective in reducing the blood glucose of a nonhuman primate (*Chlorocebus aethiops*).

The invention claimed is:

1. A method of treating diabetes type 1 or 2 in a mammal, comprising administering to a mammal in need thereof a composition comprising a therapeutically effective amount of Aspalathin to reduce blood glucose in the mammal, wherein the Aspalathin is synthetic or purified from a plant extract.

2. The method according to claim 1, wherein the Aspalathin is administered in a dosage amount of about 0.1 mg/kg/day to about 50 mg/kg/day.

3. The method according to claim 1, wherein Aspalathin is administered in a dosage amount of about 0.1 mg/kg/day to about 50 mg/kg/day.

4. The method according to claim 1, the composition further comprising a therapeutically effective amount of rutin, wherein the combination of Aspalathin and rutin reduces blood glucose in the mammal.

5. The method according to claim 4, wherein the composition comprises a molar ratio of Aspalathin:rutin of about 1:1 to about 2:1.

6. The method according to claim 1, wherein the composition comprises a pharmaceutically acceptable carrier or excipient.

7. A method of treating diabetes type 1 or 2 in a mammal, comprising administering to a mammal in need thereof a therapeutically composition comprising a therapeutically effective amount of Aspalathin enriched plant extract from an unfermented plant of the genus *Aspalathus* to reduce blood glucose in the mammal.

8. The method of claim 7, wherein the extract is an alcohol extract.

9. The method of claim 7, wherein the plant comprises *Aspalathus linearis*.

10. The method according to claim 7, wherein the Aspalathin enriched extract is administered in a dosage amount of from about 0.1 mg/kg/day to about 50 mg/kg/day.

11. The method according to claim 7, wherein the composition further comprises rutin.

12. The method according to claim 7, wherein the Aspalathin enriched extract is in a concentrated and dried form.

13. The method according to claim 7, wherein the composition comprises a pharmaceutically acceptable carrier or excipient.

14. The method according to claim 7, wherein the composition comprises a molar ratio of Aspalathin:rutin of at least 2:1.

* * * * *